(12) United States Patent
Steger

(10) Patent No.: US 10,595,947 B2
(45) Date of Patent: Mar. 24, 2020

(54) SURGICAL INSTRUMENT SHAFT WITH EMBEDDED OPTICAL FIBER

(71) Applicant: Intuitive Surgical Operations, Inc., Sunnyvale, CA (US)

(72) Inventor: John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 16/192,315

(22) Filed: Nov. 15, 2018

(65) Prior Publication Data

US 2019/0151036 A1    May 23, 2019

Related U.S. Application Data

(60) Provisional application No. 62/588,081, filed on Nov. 17, 2017.

(51) Int. Cl.

| | |
|---|---|
| *G02B 6/06* | (2006.01) |
| *A61B 34/35* | (2016.01) |
| *A61B 34/00* | (2016.01) |
| *A61B 90/00* | (2016.01) |
| *A61B 34/20* | (2016.01) |
| *A61B 17/00* | (2006.01) |
| *A61B 34/30* | (2016.01) |
| *A61B 34/37* | (2016.01) |

(52) U.S. Cl.
CPC .............. *A61B 34/35* (2016.02); *A61B 34/20* (2016.02); *A61B 34/76* (2016.02); *A61B 90/361* (2016.02); *A61B 34/37* (2016.02); *A61B 2017/00017* (2013.01); *A61B 2017/00398* (2013.01); *A61B 2017/00477* (2013.01); *A61B 2034/2061* (2016.02); *A61B 2034/305* (2016.02); *A61B 2090/064* (2016.02); *A61B 2090/065* (2016.02); *A61B 2090/0811* (2016.02); *A61B 2090/3614* (2016.02)

(58) Field of Classification Search
CPC ....... A61B 1/07; A61B 1/00096; A61B 34/35; G02B 6/06; G02B 23/2469
See application file for complete search history.

(56) References Cited

U.S. PATENT DOCUMENTS

| | | | |
|---|---|---|---|
| 7,867,241 B2* | 1/2011 | Brock ................ | A61B 17/0469 600/114 |
| 8,459,138 B2* | 6/2013 | Zubiate ..................... | B25J 9/06 74/490.04 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Jennifer Doan
(74) *Attorney, Agent, or Firm* — Schwegman Lundberg & Woessner, P.A.

(57) ABSTRACT

A surgical instrument shaft is provided that includes a hollow tube formed of a base material and including an inner wall surface and an outer wall surface; reinforcing glass material is embedded between the inner surface and outer wall surface; an optical fiber is embedded within the base material between the inner wall surface and the outer wall surface.

20 Claims, 10 Drawing Sheets

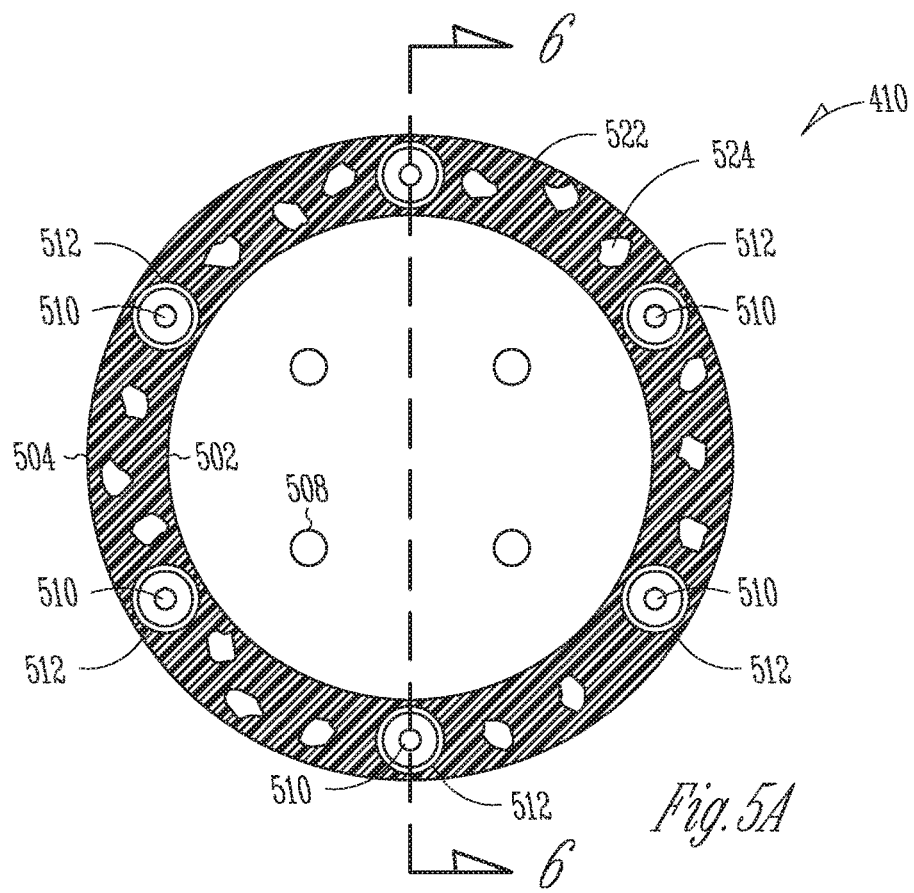
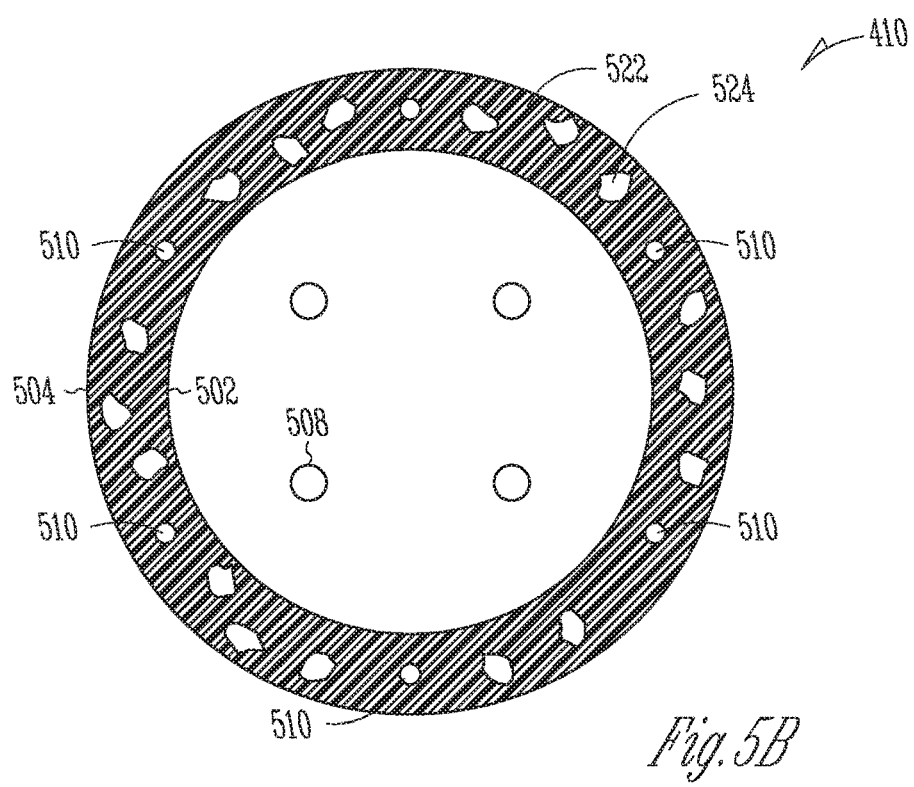

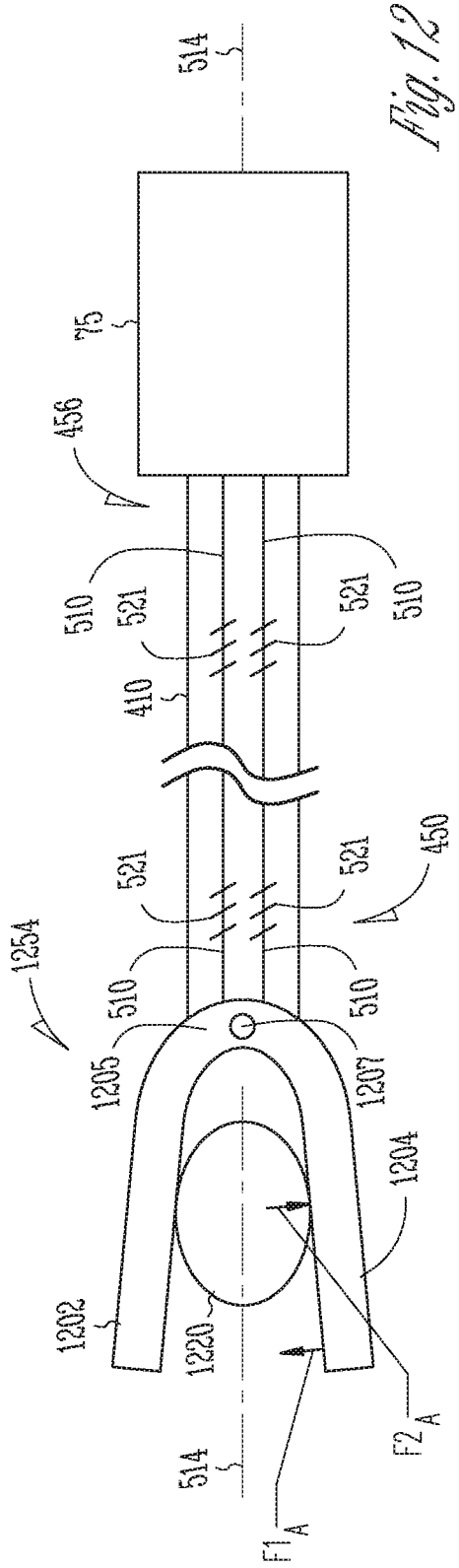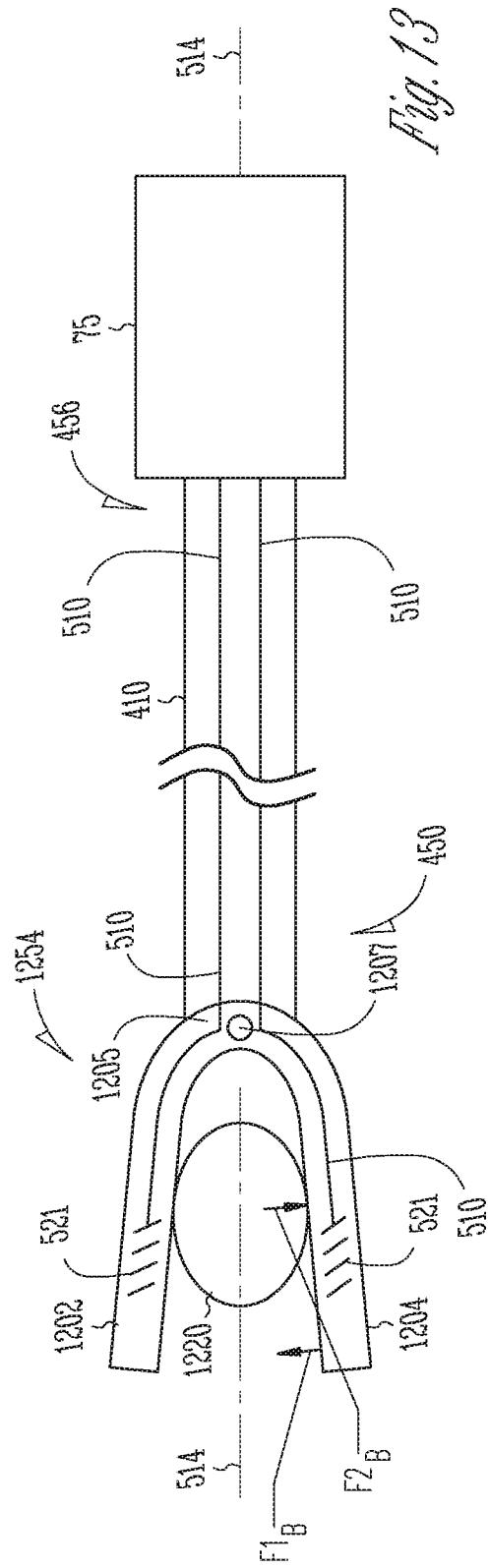

SURGICAL INSTRUMENT SHAFT WITH EMBEDDED OPTICAL FIBER

CLAIM OF PRIORITY

This application claims the benefit of priority under 35 U.S.C. § 119(e) to U.S. Provisional Patent Application Ser. No. 62/588,081, filed on Nov. 17, 2017, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances. In manual minimally invasive surgery, surgeons feel the interaction of the instrument with the patient via a long shaft, which eliminates tactile cues and masks force cues. In teleoperation surgery systems, natural force feedback is largely eliminated because the surgeon no longer manipulates the instrument directly. Kinesthetic or force feedback systems typically measure or estimate the forces applied to the patient by the surgical instrument.

SUMMARY

In one aspect, a surgical instrument shaft is provided that includes a hollow tube including an inner wall surface and an outer wall surface. The hollow tube is formed from a base material. Reinforcing glass material is embedded between the inner surface and outer wall surface. An optical fiber is embedded within the base material between the inner wall surface and the outer wall surface.

In another aspect, a surgical instrument is provided that includes a hollow tubular shaft including a distal end portion and a proximal end portion. The shaft is formed of a base material and includes an inner wall surface and an outer wall surface. Reinforcing glass is embedded therein between the inner wall surface and the outer wall surface. The inner wall surface defines a lumen that extends between the distal end portion and the proximal end portion. An optical fiber is disposed between the inner wall surface and the outer wall surface and extenda between the distal end portion and the proximal end portion. An end effector is disposed at the distal end portion of the shaft. A carriage is disposed at the proximal end of the shaft. A a cable extends within the lumen between the end effector and the carriage.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 5A is an illustrative end cross-section view of the surgical instrument shaft with optical fibers inserted within glass tubules embedded within the shaft wall.

FIG. 5B is an illustrative end cross-section view of the surgical instrument shaft with optical fibers embedded directly within the shaft wall.

FIG. 12 is an illustrative drawing showing an example force exerted upon a surgical instrument shaft having FBG strain sensors formed within optical fiber within the shaft.

FIG. 13 is an illustrative drawing showing an example external force exerted upon an end effector having an optical fiber thereon that contains an FBG strain sensor.

DESCRIPTION OF EMBODIMENTS

Teleoperated Surgical System

Figure 1:
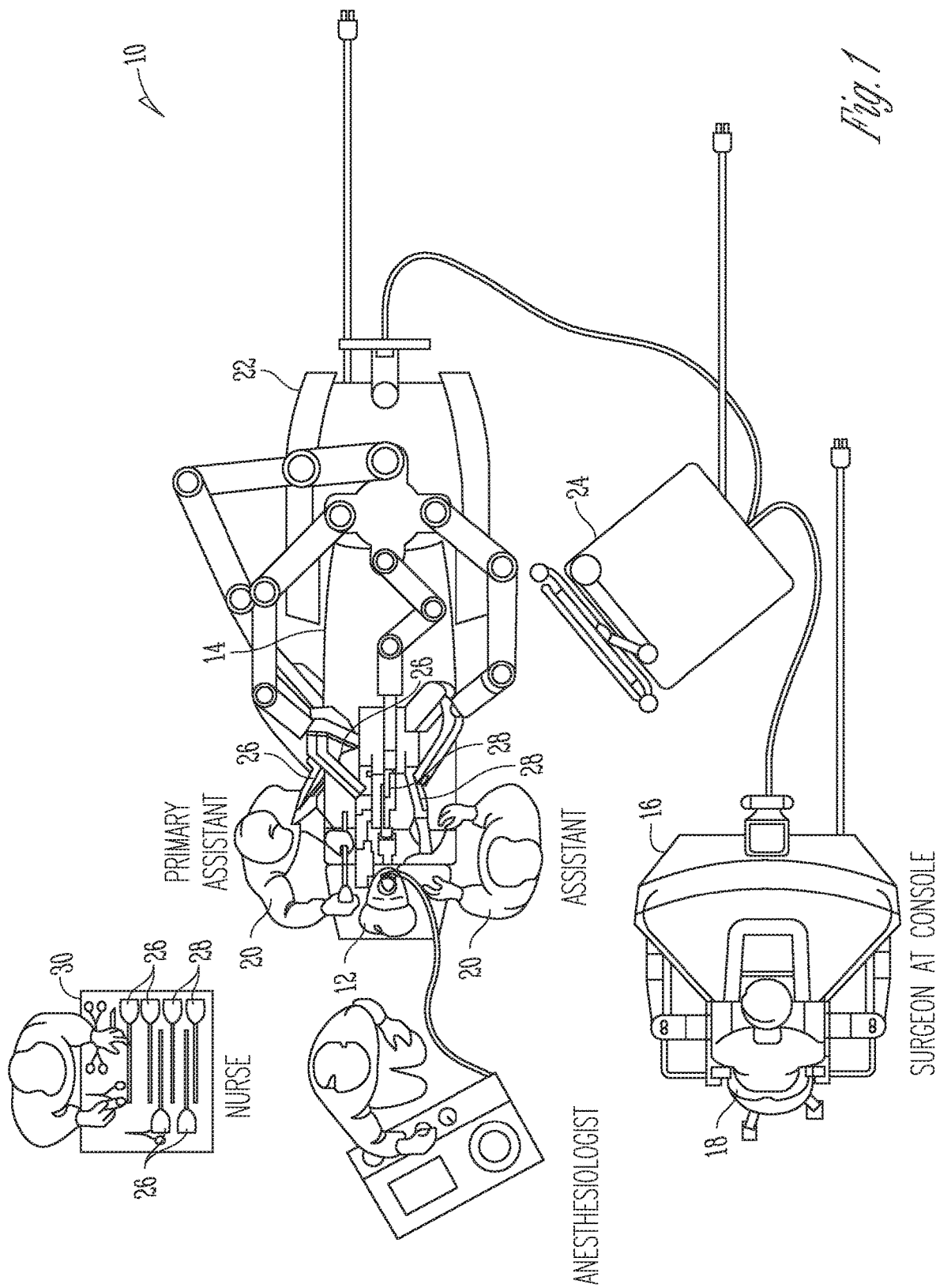
FIG. 1 is an illustrative plan view of a minimally invasive teleoperated surgical system.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 also may participate in the procedure. The minimally invasive teleoperated surgical system 10 further includes one or more patient-side carts 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
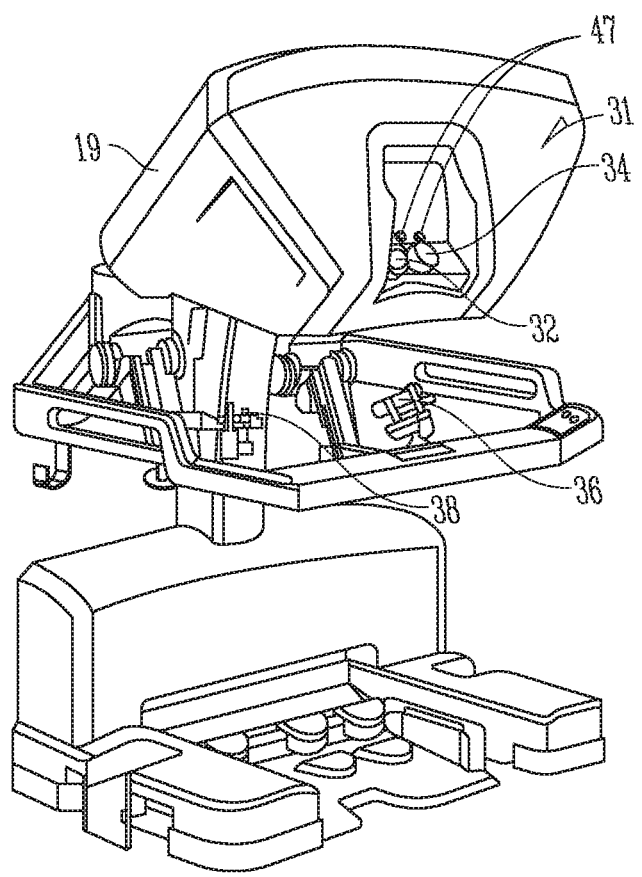
FIG. 2 is a perspective view of the surgeon's console of the minimally invasive teleoperated surgical system of FIG. 1.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive the larger-scale hand control movements. One or more surgical instruments installed for use on the patient-side cart 22 move in smaller-scale distances in response to surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints.

Figure 3:
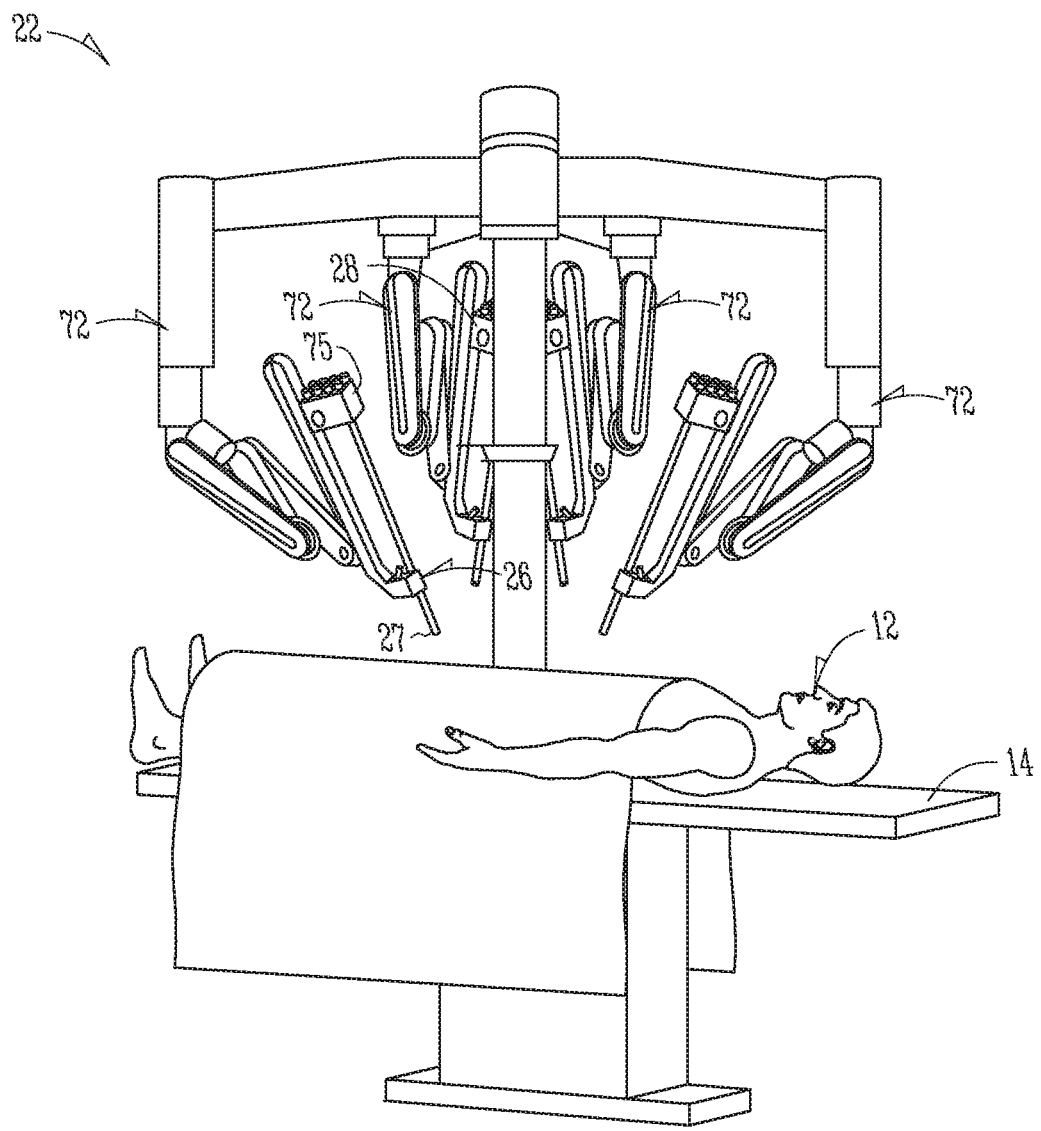
FIG. 3 is a perspective view of a patient-side cart of a minimally invasive teleoperated surgical system of FIG. 1.

FIG. 3 is a perspective view of a patient-side cart 22 of a minimally invasive teleoperated surgical system 10, in accordance with some embodiments. The patient-side cart 22 includes four mechanical support arms 72. A surgical instrument carriage 75, which includes instrument motors to control instrument motion, is mounted at the end of each support arm assembly 72. Additionally, each support arm 72 can optionally include one or more setup joints (e.g., unpowered and/or lockable) that are used to position the attached surgical instrument carriage 75 in relation to the patient for surgery. The surgical instrument 26 is detachably connected to the instrument carriage 75. While the patient-side cart 22 is shown as including four surgical instrument carriages 75, more or fewer surgical instrument carriages 75 may be used. A teleoperated surgical system will generally include a vision system that typically includes an endoscopic camera instrument 28 for capturing video images and one or more video displays for displaying the captured video images.

In one aspect, for example, individual surgical instruments 26 and cannulas 27 are removably coupled to the carriages 75, with the surgical instrument 26 inserted through the cannula 27. One or more teleoperated actuator motors of the carriages 75 move the surgical instrument 26 as a whole. In one aspect, the instrument carriage 75 houses one or more teleoperated actuator motors (not shown) inside that provide a number of controller motions that the surgical instrument 26 translates into a variety of movements of an end effector on the surgical instrument 26. Thus, the teleoperated actuator motors in the instrument carriage 75 move individual components of the surgical instrument 26 such as end effector wrist movement or jaw movement, for example.

Inputs to control an instrument's individual components are such that the input provided by a surgeon or other medical person to the control input (a "master" command) is translated into a corresponding action by the surgical instrument (a "slave" response). A wire cable-based force transmission mechanism or the like is used to transfer the motions of each of the remotely located teleoperated motors to a corresponding instrument-interfacing actuator output located on instrument carriage 75. In some embodiments, the surgical instrument 26 is mechanically coupled to a first actuator motor, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of jaws of an end effector, for example.

Figure 4:
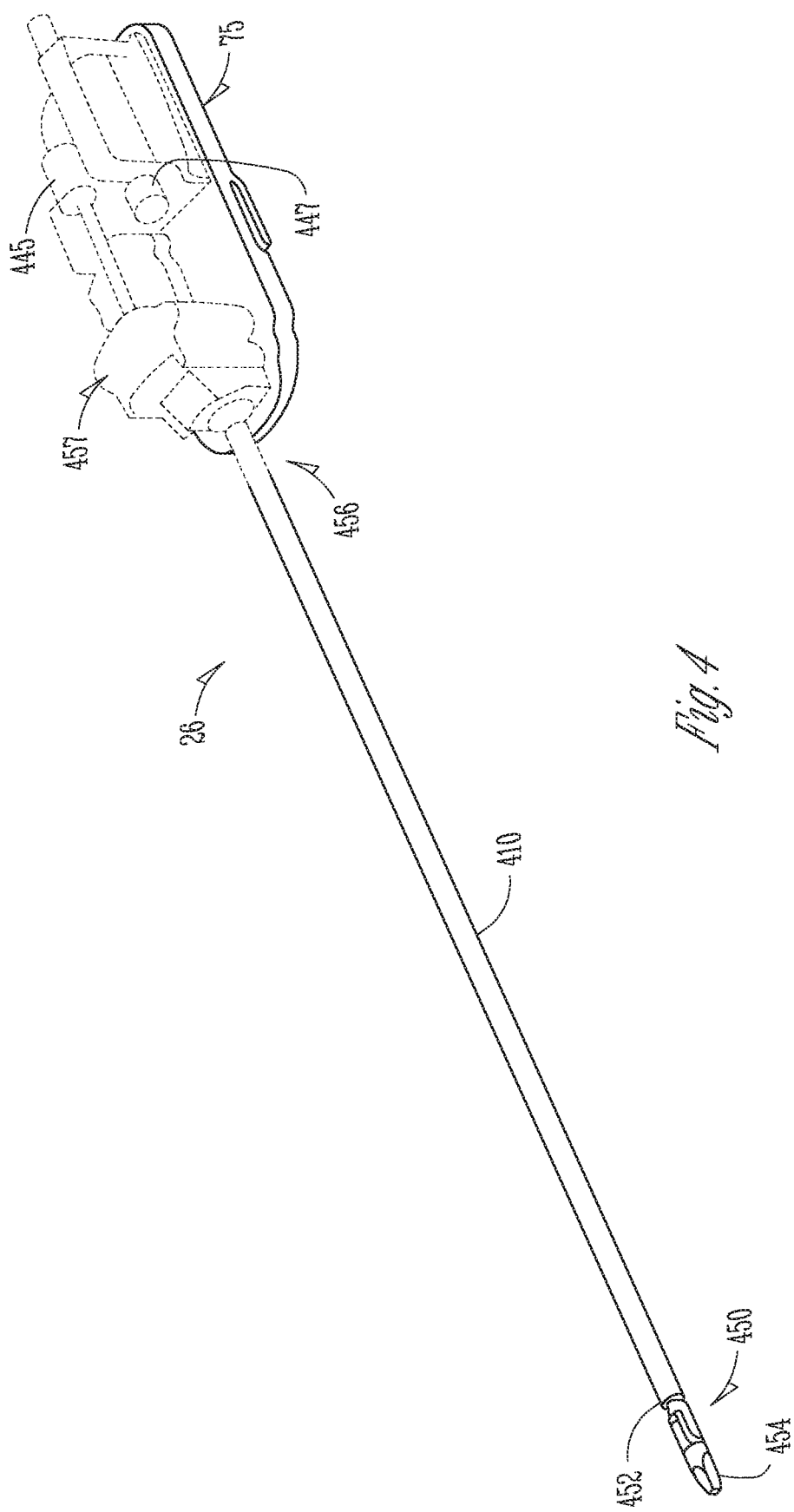
FIG. 4 is a perspective view of a surgical instrument used with the minimally invasive teleoperated surgical system of FIG. 1.

FIG. 4 is a perspective view of a surgical instrument 26, which includes an elongated hollow cylindrical tubular shaft 410 having a distal (first) end portion 450 for insertion into a patient's body cavity and proximal (second) end portion 456 that includes a wire coupler 457, which may include one or more pulleys, guides, anchors, capstans levers or linear slides, to operatively mechanically couple wires to one or more motors 445, 447 (shown with dashed lines), within an instrument carriage 75, to exert force upon wire cables (not shown). The wires are operatively coupled so that movement of the wires may impart motion to an end effector 454 such as to open or close of jaws and (x, y) wrist motion, for example. The surgical instrument 26 is used to carry out surgical or diagnostic procedures. The distal portion 450 of the surgical instrument 26 can provide any of a variety of end effectors 454, such as the forceps, a needle driver, a cautery device, a cutting tool, an imaging device (e.g., an endoscope or ultrasound probe), or the like. A surgical end effector 454 can include a functional mechanical degree of freedom, such as jaws that open or close, or a knife that translates along a path or a wrist that may move in x and y directions. Thus, the motors 445, 447 located at the carriage 75 near the proximal end portion 456 of the shaft 410 control movement of the end effector 454 at the distal end portion 450 of the shaft 410 by exerting forces upon wires (not shown) extending within the shaft 410 between the motors and the end effector.

Tubular Instrument Shaft with Embedded Optical Fiber

Figure 6:
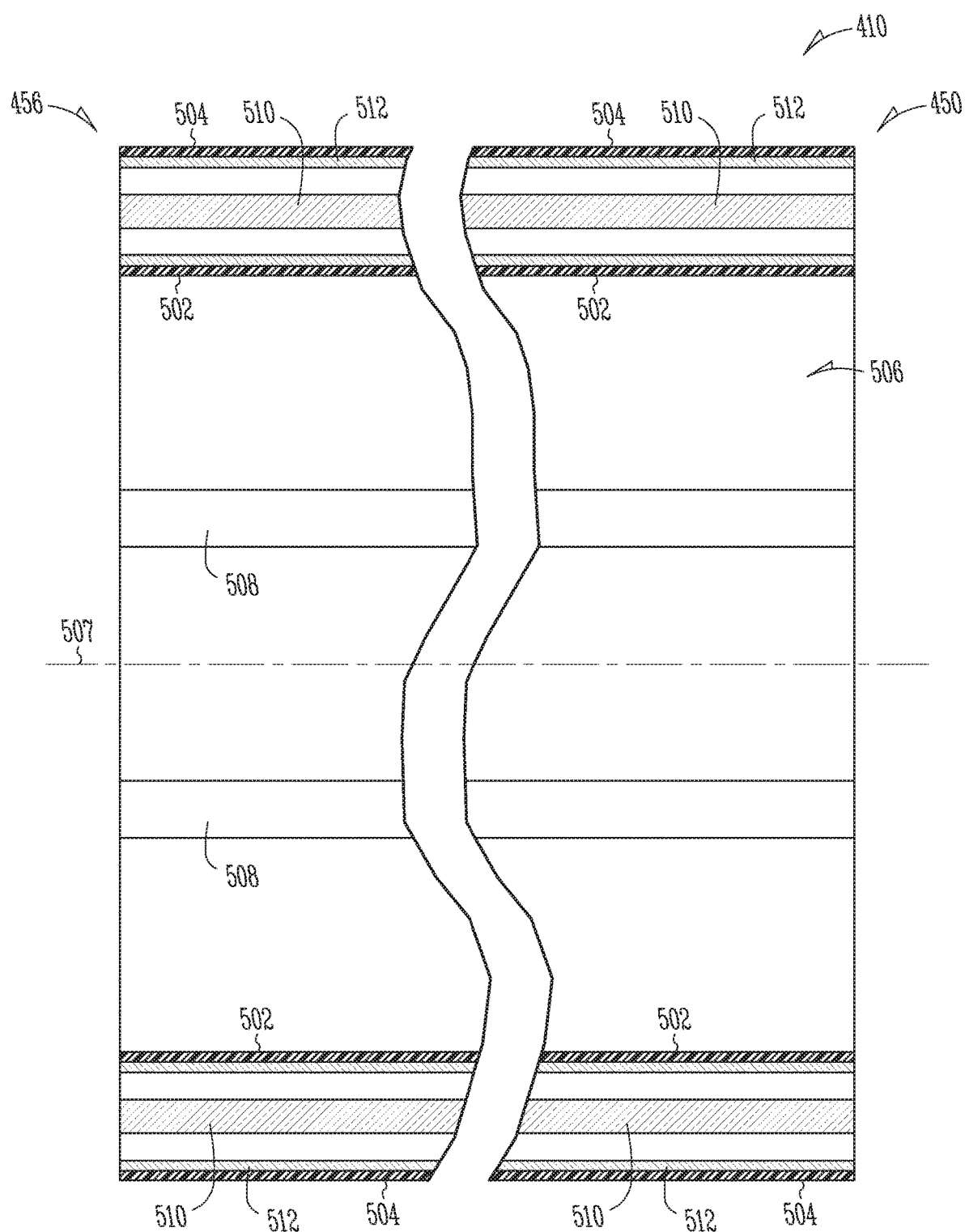
FIG. 6 is an illustrative side cross-section view of the surgical instrument shaft.

FIG. 5A is an illustrative end cross-section view of the surgical instrument shaft 410 with optical fibers 510 inserted within glass tubules 512 embedded within the shaft wall. FIG. 6 is an illustrative side cross-section view of the surgical instrument shaft 410. Referring to FIGS. 5A-6, the surgical instrument shaft 410 includes an elongated hollow cylindrical tube with an internal tubular wall surface 502 and an external tubular wall surface 504 and a uniform tubular wall thickness. The internal tubular wall surface 502 of the shaft 410 defines an internal center lumen 506. The shaft 410 has a longitudinal center axis 507. Wire cables extend 508 within the lumen 506 to control the movement of a surgical instrument end effector (not shown) disposed at one end of the shaft 410. In some embodiments, the shaft 410 has a length of about twenty-two inches and a diameter of about eight millimeters. Reinforcing glass material 524 includes roving glass fiber strands is embedded within the shaft 410 between the inner and outer tubular wall surfaces 502, 504. A plurality of elongated optical fibers 510 are inserted within hollow glass tubules 512 that are embedded within the shaft 410 between the inner and outer tubular wall surfaces 502, 504 and extend longitudinally along the entire the length of the shaft. The tubules 512 have an inner wall diameter that is greater than the diameter of the optical fibers 510 extending within them to provide spacing tolerance between them so that the optical fibers 510 may be inserted into the glass tubules 512 following a pultrusion manufacturing process described below. Some advantages of insertion of fibers 510 within tubules 512 is reduction of risk of damage to optical fiber during pultrusion and the ability to test and replace optical fibers within tubules.

FIG. 5B is an illustrative end cross-section view of the surgical instrument shaft 410 with optical fibers 510 embedded directly within the shaft wall. In the alternative embodiment, the optical fibers 510 are embedded directly within the shaft 410 (with no tubules) during the pultrusion process, between the inner and outer tubular wall surfaces 502, 504 and extend longitudinally along the entire the length of the shaft. Thus, there is no need to insert optical fibers 510 within tubules following pultrusion.

Figure 7:
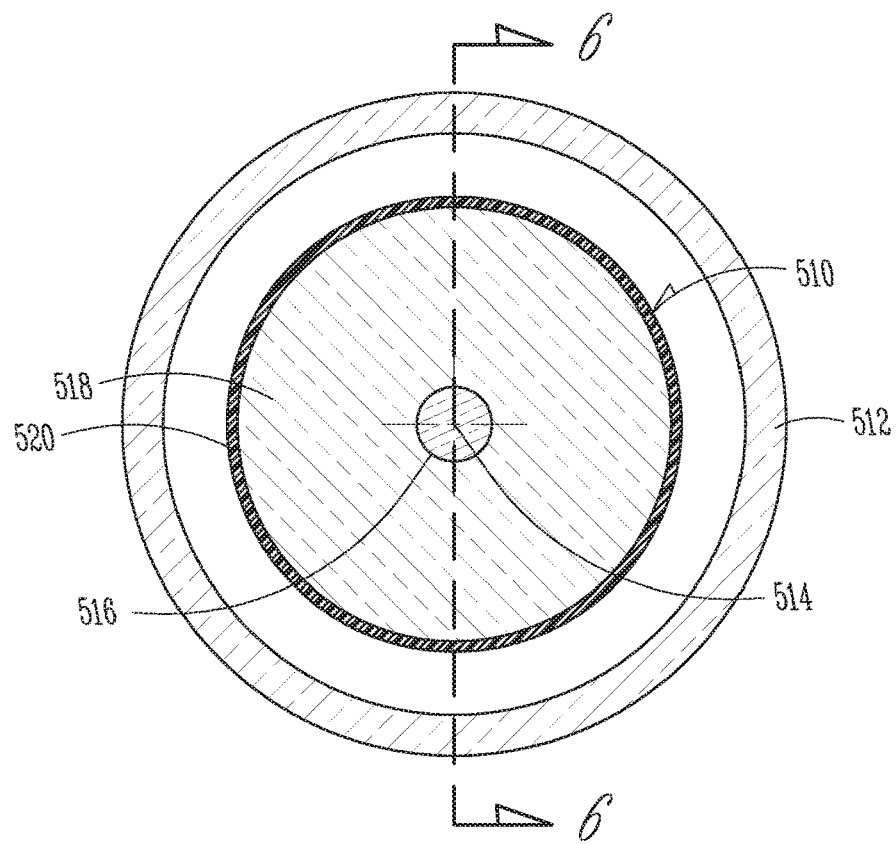
FIG. 7 is an illustrative end cross-section view of an optical fiber inserted within a hollow glass tubule embedded within the shaft.
Figure 8:
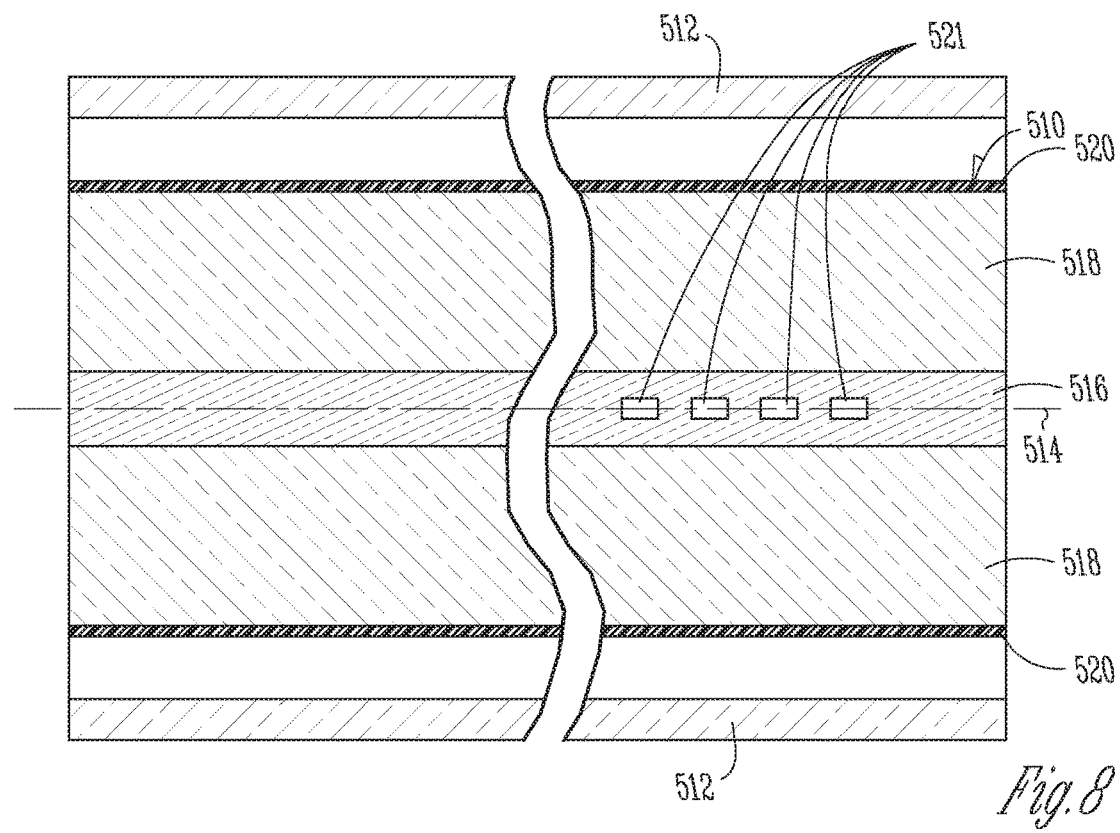
FIG. 8 is an illustrative side cross-section view of an optical fiber inserted within a hollow glass tubule embedded within the shaft.

FIG. 7 is an illustrative end cross-section view of an optical fiber 510 inserted within a hollow glass tubule 512 embedded within the shaft 410. FIG. 8 is an illustrative side cross-section view of the optical fiber 510 inserted within the hollow glass tubule 512 embedded within the shaft 410. Referring to FIGS. 7-8, the optical communication fibers 510 act as a cylindrical dielectric waveguides that transmit light 514 parallel to their longitudinal center axes 514 by a process of total internal reflection. The optical fibers 510 are formed from a glass material (silica). Each optical fiber 510 includes a transparent core 516 surrounded by a transparent cladding material 518 with a lower index of refraction. The difference of refraction indexes between the inner core 516 and the cladding 518 causes the light to propagate only inside the inner core 516. In some embodiments, the core 516 has a diameter of about 5-10 microns, and the cladding 518 has a diameter of about 50-125 microns. The optical fibers 510 also may include a protective outer buffer layer 520 such as an acrylic or polyimide material to is protect against water and hydrogen which otherwise may promote crack growing and reduce mechanical stability. Fiber Bragg grating (FBGs) 521 to act as strain sensors are formed in the optical fiber core 516 to detect bending stresses imparted to the optical fiber 510 and to the shaft 410 that has the optical fiber 510 embedded in it. Thus, the optical fibers 510 embedded between the inner and outer tubular walls 502, 504 of the shaft 410 transmit optical signals along the length of the shaft 410. Referring again to FIGS. 5A-6, the tubular shaft is formed of a matrix that includes a base material 522 and a reinforcing glass material 524. The base material 522 includes a thermosetting resin. In some embodiments, the thermosetting resin that includes an epoxy or polyester thermoplastic resin. In some embodiments, the reinforcing glass material 524 includes roving glass fiber strands embedded within the base material 522 and positioned in generally parallel relation with each other to provide mechanical strength and resistance to damage from the outside forces, and to maintain the shaft 410 in a fixed shape. In some embodiments, the roving glass fiber strands have a diameter of about twenty microns.

In some embodiments, hollow glass tubules 512 embedded within the tubular shaft 410 extend the length of the shaft. The glass tubules 512 have a thermal coefficient of expansion (TCE) that closely matches that of the reinforcing glass material 524. The glass tubules 512 are embedded within the matrix to protect the optical fibers 510 from damage during pultrusion. The optical fibers 510 may be inserted within the glass tubules 512 after the glass tubules have been embedded in the walls of the shaft 410 during pultrusion process used to produce the shaft.

Figure 9:
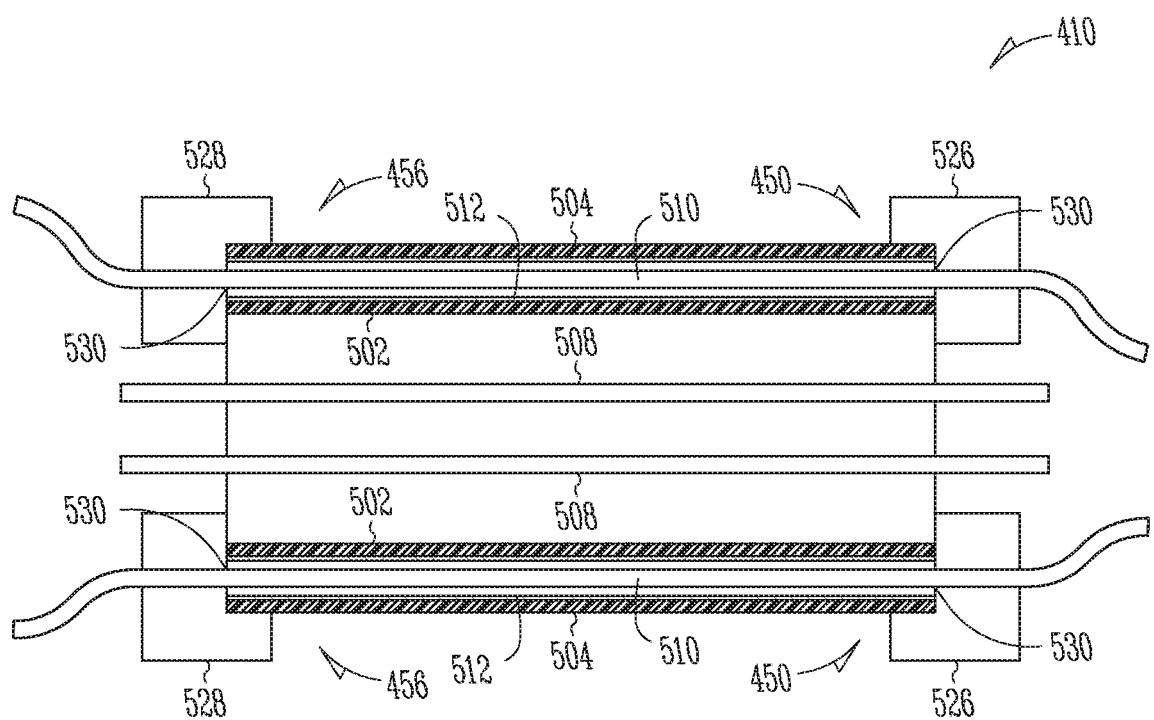
FIG. 9 is an illustrative side cross-section view of the shaft with optical signal couplers at opposites ends thereof.
Figure 10:
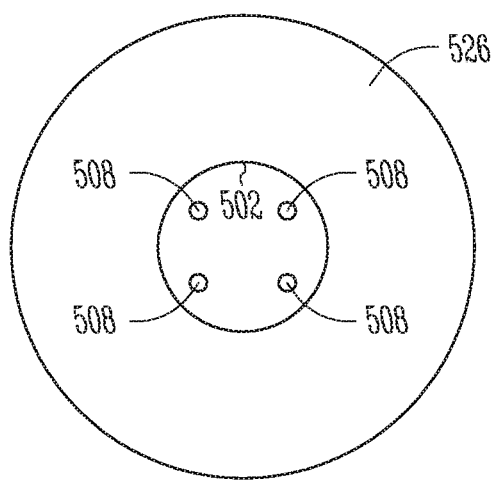
FIG. 10 is an illustrative distal end view of the shaft with the first signal optical coupler mounted thereon.

FIG. 9 is an illustrative side cross-section view of the surgical instrument shaft 410 with first and second optical signal couplers 526, 528 coupled at distal and proximal ends 450, 456 of the shaft 410. An optical coupler may reflect back light transmitted to it from an optical fiber 510 so that the reflected light may be detected by a phase shift detector (not shown) to determine stress imparted to FBG strain sensors inscribed upon the optical fiber. Alternatively, an optical coupler may terminate an optical signal transmitted to it from an optical fiber 510. FIG. 10 is an illustrative distal end view of the shaft with the first signal optical coupler 526 mounted thereon. Optical fiber end faces 530 at each end of the shaft 410 are operatively coupled to the first and second optical signal couplers 526, 528 at opposite ends of the shaft 410 to input light to and output light from the optical fibers 510. In some embodiments, the optical signal couplers 526, 528 may couple to some but not all the optical fibers 510 within the tubular walls of the shaft 410. To provide redundancy, more optical fibers 510 may be provided within the tubular walls of the shaft 410 than are required for coupling to the couplers first and second couplers 526, 528. Placement of the optical fibers within the tube walls may be imprecise. Some optical fibers may be placed at locations within the tube walls during manufacturing that are difficult to align with the optical signal couplers. Moreover, the optical fibers are fragile and easily damaged during use. Some optical fibers may be placed closer to an outer perimeter portion of the tube walls where they may be more susceptible to damage in use. The optical signal couplers may be coupled selectively to a subset of the optical fibers that are better positioned for alignment and that are more safely positioned nearer the center of the tube wall thickness.

Protrusion Process Example

Figure 11:
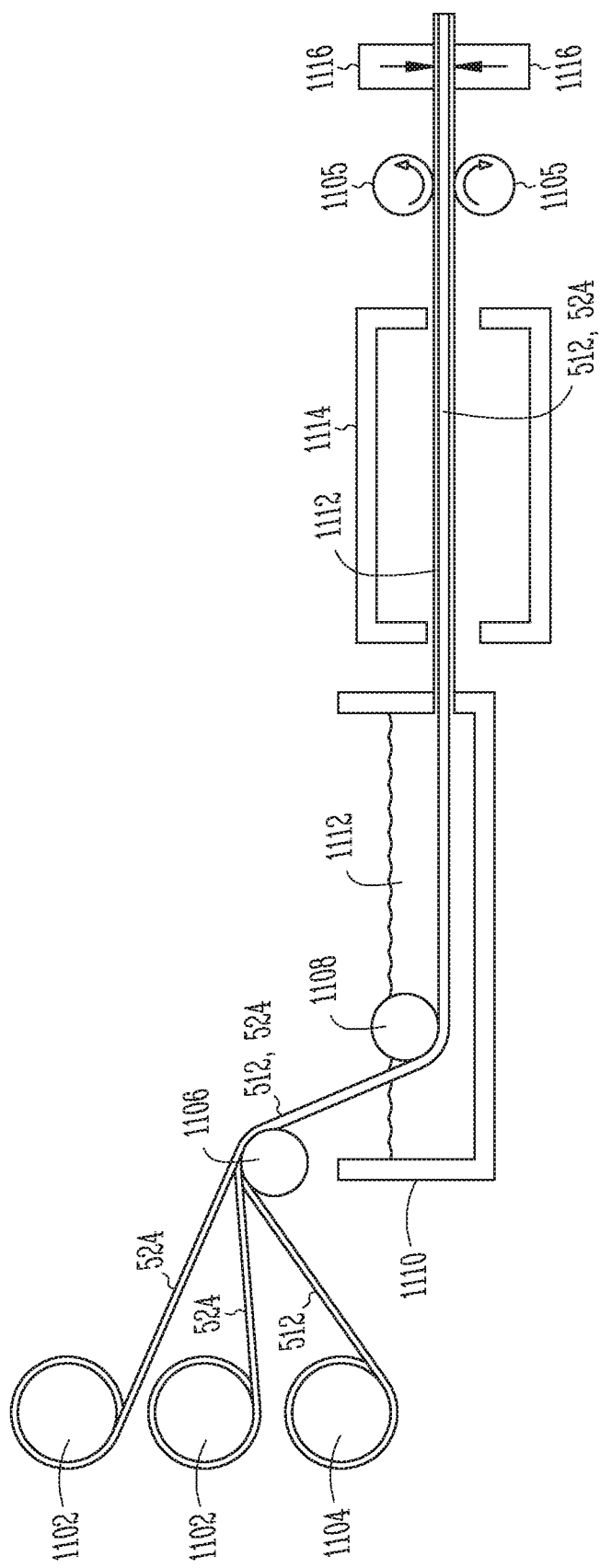
FIG. 11 is an illustrative process flow diagram representing a pultrusion process that may be used to produce the shaft.

FIG. 11 is an illustrative process flow diagram representing a pultrusion process that may be used to produce the hollow tubular instrument shaft 410. During the pultrusion process, multiple spools 1102 of continuous reinforcing glass fibers 524 and multiple spools 1104 (only one shown) of hollow glass tubules 512 are pulled through a bath of resin together with the glass tubules and then through a die. Pullers 1105 pull the hollow glass tubules 512 and reinforcing glass fibers 524, and guides or tensioners 1106, 1108 guide them through a tub 1110 containing thermosetting resin 1112. The hollow glass tubules 512 are pulled through the resin in parallel with the reinforcing glass fibers 524 so that the glass tubules 512 are distributed between the tubular walls 502, 504 of the shaft 410 with their longitudinal axes aligned with the longitudinal axis 507 of the shaft 410. During the pultrusion process, the glass tubules act as individual mandrels that remain in place following pultrusion. A heated die 1114 forces the glass hollow tubules 512 and the reinforcing glass fibers 524 and to conform to the hollow tubular shape of the shaft 410. The resin 1112 cures to set the hollow glass tubules 512 and the reinforcing glass fibers 524 into a tubular contour that is the shaft 410. During pultrusion, a diameter of the inner lumen 506 of the pultruded shaft 410 is determined by a center mandrel (not shown). After the composite shaped as a tubular shaft emerges from the die 1114, it is allowed to post-cure while being pulled to a saw 1116 where it is cut to into individual shafts 410.

Thus, during pultrusion manufacturing, the liquid resin 1112, the hollow glass tubules 512 and the reinforcing glass fibers 524 are pulled (rather than pushing, as is the case with extrusion) through the heated forming die 1114 using a continuous pulling device 1116. A gelation, or hardening, of the resin is initiated by the heat from the die 1114 and a rigid, cured profile is formed in the shape of the die 1114 to form the hollow tubular shaft. With all the reinforcing fibers 524 running unidirectionally, the pultruded tubular shaft 410 has a high stiffness to weight ratio.

Referring again to FIGS. 7-8, the multiple optical fibers 510 are inserted within the plurality of glass tubules 512 after completion of the pultrusion process. An inert lubricant, such as an FFP or PFA film may be applied to the optical fibers 510 to reduce friction during the insertion. In general, the optical fibers 510 are strong under tensile forces but may crack easily due to other forces. The insertion of the optical fibers 510 into the glass tubules 512 after the pultrusion process avoids a risk of cracking and damaging the optical fibers 510 due to external forces imparted during the pultrusion process and later, from external forces during use.

Referring again to FIGS. 4-5A, a proximal portion of the shaft 410 is held in a fixed position by a support arm 72 while an end effector 454 is disposed at the distal end 456 of the shaft 410. During use in a surgical procedure, one or more motors 445, 447 disposed at the proximal end 450 of the shaft 410 imparts axial forces to wire cables 508, shown in FIGS. 5A-6, extending within the center lumen 506 of the shaft 410 to control movement of an end effector 454 disposed at the distal end 450 of the shaft 410. The end effector 454 may include a gripper, for example, and the end effector movement may include opening and closing of gripper jaws. Alternatively, for example, the end effector 454 may include a knife, and the end effector movement may include dissecting or cutting.

External Force Examples

FIG. 12 is an illustrative drawing showing an example external force exerted upon a surgical instrument shaft 410 having FBG strain sensors 521 formed within optical fiber within the shaft 410. A cantilever end effector 1254 at a distal end portion 450 of the shaft includes first and second jaws 1202, 1204 mounted at a clevis 1205 at a distal end portion of the shaft 410 to articulate between open and closed positions about a pivot 1207. A proximal end portion 456 of the shaft 410 has a fixed position at an instrument carriage 75. In the example of FIG. 12, one or more motors 445, 447 within the carriage 75 impart force to wires 508 within the hollow shaft 410 to cause a movement of the jaws 1202, 1204 that imparts a first external force $F1_A$ upon anatomical tissue 1220 to urge it in an upward direction. It is assumed in this example that the tissue exerts a counter-force $F2_A$ in a downward direction that resists the first force $F1_A$. The end effector 1254 is coupled to the distal end portion 450 of the shaft 410 to transmit the second external tissue force $F2_A$ to the distal end portion 450 of the shaft 410. The second external force $F2_A$ imparted to the end effector 1254 includes a force component that is perpendicular to the longitudinal axis 514 of the shaft 410. Since the proximal end portion 456 of the shaft 410 is fixed at the carriage 75, a force component of the second force $F2_A$ that is perpendicular to the longitudinal axis 514 of the shaft imparts a bending stress to the shaft 410.

Bending stress imparted to the shaft also may be imparted to FBG strain sensors 521 formed in the optical fibers 510 extending longitudinally within the tubular shaft 410. A FBG reflects a wavelength of light that shifts in response to variations in temperature and/or strain. Broadband light may be injected via an optical signal coupler 526, 528 to the optical fibers 510 embedded within the tubular shaft 410. The wavelength of light reflected by the FBG strain sensors 521 formed in the optical fibers varies with stress imparted to the FBG strain sensors. The optical fibers 510 are distributed circumferentially within the tubular shaft 410 so that while a compressing stress is imparted to an FBG strain sensor within an optical fiber in one circumferential portion of the tubular shaft 410, a tensile stress may be imparted to an FBG strain sensor within an optical fiber located in a different circumferential portion of the tube wall, such as a diametrically opposite circumferential portion of the tube wall. Thus, the FBG strain sensors embedded within the tubular shaft 410 may be used to determine direction and magnitude of external forces imparted to an end effector 1254 by anatomical tissue, for example.

FIG. 13 is an illustrative drawing showing an example external force exerted upon an end effector 1254 having optical fibers 510 thereon that each contains an FBG strain sensor 521. The end effector 1254 is disposed at a distal end portion of a tubular surgical instrument shaft 410. The optical fibers 510 extends between inner and outer walls 502, 504 of the tubular surgical instrument shaft 410 and also extends beyond the shaft 410 and onto the end effector 1254. In the embodiment of FIG. 13, multiple FBG strain sensors 521 are disposed at the end effector 1254. More particularly, multiple FBG strain sensors 521 are located within the each of the first and second cantilever jaws 1202, 1204 mounted at a clevis 1205 at a distal end portion of the shaft 410 to articulate between open and closed positions about a pivot 1207. An example first external force $F1_B$ is imparted by the jaws 1202, 1204 upon anatomical tissue 1220 to urge the anatomical tissue 1220 in an upward direction. It is assumed in this example that the tissue exerts a counter-force $F2_B$ in a downward direction that resists the first force $F1_B$. Optical fibers 510 embedded within the tubular shaft 410 propagate broadband light to the FBG strain sensors 521 disposed at the end effector jaws 1202, 1204. The light wavelength reflected back by jaw-mounted FBG strain sensor 521 may vary with stress imparted to one or both of the first and second jaws 1202, 1204 by the second force $F2_B$. Thus, the light wavelength reflected back to the optical fibers 510 by one or more of the end effector mounted FBG strain sensors 521 is indicative of stress imparted to the end effector 1254 by the second force $F2_B$.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein. The above description is presented to enable any person skilled in the art to create and use a surgical instrument shaft with embedded optical fiber. Various modifications to the embodiments will be readily apparent to those skilled in the art, and the generic principles defined herein may be applied to other embodiments and applications without departing from the spirit and scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. A surgical instrument shaft comprising:
    a hollow tube including an inner wall surface and an outer wall surface comprising: a base material having a reinforcing glass material embedded therein between the inner surface and outer wall surface; and
    an optical fiber embedded within the base material between the inner wall surface and the outer wall surface.

2. The surgical instrument shaft of claim 1 further including:
    a glass tubule embedded within the resin material between the inner wall surface and the outer wall surface;
    wherein the optical fiber is disposed within the glass tubule.

3. The surgical instrument shaft of claim 1 further including:
    a lubricant material disposed between the optical fiber and the glass tubule.

4. The surgical instrument shaft of claim 1 further including:
    a protective buffer layer about the optical fiber; and
    a lubricant material disposed between the protective buffer layer and the glass tubule.

5. The surgical instrument shaft of claim 1,
    wherein the base material includes a resin.

6. The surgical instrument shaft of claim 1,
    wherein the reinforcing glass material includes reinforcing glass fibers.

7. The surgical instrument shaft of claim 1 further including:
    a plurality of optical fibers embedded within the base material between the inner wall surface and the outer wall surface.

8. The surgical instrument shaft of claim 1 further including:
    a fiber Bragg grating formed in the optical fiber.

9. The surgical instrument shaft of claim 1 further including:
    a plurality of optical fibers embedded within the base material between the inner wall surface and the outer wall surface;
    a fiber Bragg grating formed in two or more of the optical fibers;
    wherein the two or more optical fibers are distributed circumferentially between the inner wall surface and the outer wall surface such that when a compressing stress is imparted to fiber Bragg gratings within an optical fiber in one circumferential portion of the hollow tube, a tensile stress is imparted to fiber Bragg gratings within an optical fiber located in a different circumferential portion of the tube wall.

10. The surgical instrument of claim 1 further including:
    an optical signal coupler disposed at at least one end of the hollow tube, operatively coupled the end face of optical fiber.

11. A surgical instrument comprising:
    a hollow tubular shaft including a distal end portion and a proximal end portion, including an inner wall surface and an outer wall surface, and including a base material having reinforcing glass embedded therein between the inner wall surface and outer wall surface; wherein the inner wall surface defines a lumen that extends between the distal end portion and the proximal end portion;
    an optical fiber disposed between the inner wall surface and the outer wall surface and extending between the distal end portion and the proximal end portion;
    an end effector at the distal end portion of the shaft;
    a carriage at the proximal end of the shaft; and
    a cable (508) extending within the lumen between the end effector and the carriage.

12. The surgical instrument of claim 11 further including:
    a glass tubule embedded within the resin material between the inner wall surface and the outer wall surface;
    wherein the optical fiber is disposed within the glass tubule.

13. The surgical instrument of claim 11,
    wherein the base material includes a resin.

14. The surgical instrument of claim 11,
    wherein the reinforcing glass material includes reinforcing glass fibers.

15. The surgical instrument of claim 11 further including:
    a plurality of optical fibers embedded within the base material between the inner wall surface and the outer wall surface.

16. The surgical instrument of claim 11 further including:
    a fiber Bragg grating formed in the optical fiber.

17. The surgical instrument of claim 11 further including:
    a plurality of optical fibers embedded within the base material between the inner wall surface and the outer wall surface;
    a fiber Bragg grating formed in two or more of the optical fibers;
    wherein the two or more optical fibers are distributed circumferentially between the inner wall surface and the outer wall surface such that when a compressing stress is imparted to fiber Bragg gratings within an optical fiber in one circumferential portion of the hollow tube, a tensile stress is imparted to fiber Bragg gratings within an optical fiber located in a different circumferential portion of the tube wall.

18. The surgical instrument of claim 11,
    wherein the optical fiber extends onto the end effector;
    further including:
    a fiber Bragg grating formed in a portion of the optical fiber that extends onto the end effector.

19. The surgical instrument of claim 11,
    wherein the optical fiber extends onto the end effector;
    wherein the end effector includes first and second jaws;
    further including:
    a fiber Bragg grating formed in a portion of the optical fiber that extends onto at least one of the first and second jaws.

20. The surgical instrument of claim 11 further including:
    an optical signal coupler disposed at at least one end of the hollow tube, operatively coupled the end face of optical fiber.

* * * * *